US010292382B2

(12) United States Patent
Bouaita et al.

(10) Patent No.: US 10,292,382 B2
(45) Date of Patent: May 21, 2019

(54) NO-SPIN CRYOPRESERVATION TECHNIQUE AND RESULTING PRODUCTS

(71) Applicant: Biopredic International, Saint-Grégoire (FR)

(72) Inventors: Belkacem Bouaita, Rennes (FR); Sandrine Camus, Langan (FR); Nathalie Rougier, Melesse (FR); Ruo Ya Li, Rennes (FR); Christophe Chesne, Vannes (FR); David M. Steen, Overland Park, KS (US)

(73) Assignee: Biopredic International Sarl, Saint-Grégoire (FR)

( * ) Notice: Subject to any disclaimer, the term of this patent is extended or adjusted under 35 U.S.C. 154(b) by 114 days.

(21) Appl. No.: 15/300,985

(22) PCT Filed: Apr. 1, 2015

(86) PCT No.: PCT/IB2015/052404
§ 371 (c)(1),
(2) Date: Sep. 30, 2016

(87) PCT Pub. No.: WO2015/151047
PCT Pub. Date: Oct. 8, 2015

(65) Prior Publication Data
US 2017/0020128 A1     Jan. 26, 2017

Related U.S. Application Data (60) Provisional application No. 61/974,702, filed on Apr. 3, 2014.

(51) Int. Cl.
A01N 1/02     (2006.01)
G01N 1/38     (2006.01)
G01N 1/42     (2006.01)

(52) U.S. Cl.
CPC ......... *A01N 1/0284* (2013.01); *A01N 1/0221* (2013.01); *G01N 1/38* (2013.01); *G01N 1/42* (2013.01)

(58) Field of Classification Search
None
See application file for complete search history.

(56) References Cited

U.S. PATENT DOCUMENTS

2004/0242495 A1* 12/2004 Staines ............... A01N 1/02
                                                  514/23
2015/0072423 A1*  3/2015 Li ..................... A01N 1/0221
                                                  435/374

FOREIGN PATENT DOCUMENTS

| EP | 0834252 | 4/1998 |
| EP | 1471140 | 10/2004 |
| WO | 02076206 | 10/2002 |

OTHER PUBLICATIONS

Hanna et al., rganogenesis 5(3):134-137 (2009).*
Patten, BD Biosciences, PowerPoint (2010) (Year: 2010).*
Terry et al., Liver Transplant., 16:229-237 (2010) (Year: 2010).*
PCT/IB2015/052404 International Search Report and Written Opinion dated Jul. 28, 2015.
Barker, et al., "A "No-wash" Albumin-Dextran Dilution Strategy for Cord Blood Unit Thaw: High Rate of Engraftment and a Low Incidence of Serious Infusion Reactions," American Society for Blood and Marrow Transplantation, vol. 15, 2009, pp. 1596-1602.
Moroff, et al., "Retention of cellular properties of PBPCs following liquid storage and cryopreservation," Transplantation and Cellular Engineering, vol. 44, 2004, pp. 245-252.
Regan, et al., "Comparison of cord blood thawing methods on cell recovery, potency, and infusion," Transplantation and Cellular Engineering, vol. 50, 2010, pp. 2670-2675.
Terry, et al., "Optimization of the Cryopreservation and Thawing Protocol for Human Hepatocytes for Use in Cell Transplantation," Liver Transplantation, vol. 16, 2010, pp. 229-237.
Kielberg, et al., "Cryopreservation of Mammalian Cells—Protocols," Thermo Scientific, vol. 14, 2010, 2 pages.
Meng, et al., "An improved purification approach with high cell viability and low cell loss for cryopreserved hepatocytes," Cryobiology, vol. 60, 2010, pp. 238-239.

* cited by examiner

*Primary Examiner* — Thomas J. Visone
(74) *Attorney, Agent, or Firm* — Hovey Williams LLP (57) ABSTRACT

Methods and processes for cryopreservation and direct cell thawing and seeding or suspension after cryopreservation, including methods that eliminate the necessity of post-thaw wash, spin, and frequent practice of performing a cell count. Cell compositions and no-spin cell products produced using the methods are also described.

16 Claims, 9 Drawing Sheets

Fig. 1

| Cell morphology | Classical freezing and thawing method HPR116-S | Improved freezing and thawing method HPR116-NS |
|---|---|---|
| 6 hours |  |  |
| Day 7 |  |  |

NO-SPIN CRYOPRESERVATION TECHNIQUE AND RESULTING PRODUCTS

CROSS-REFERENCE TO RELATED APPLICATIONS

The present application is the National Stage of International Patent Application No. PCT/IB/2015/052404, filed Apr. 1, 2015, entitled NO-SPIN CRYOPRESERVATION TECHNIQUE AND RESULTING PRODUCTS, which claims the priority benefit of U.S. Provisional Patent Application Ser. No. 61/974,702, filed Apr. 3, 2014, entitled A FREEZING PROCESS THAT ALLOWS DIRECT THAWING AND SEEDING OF CRYOPRESERVED DIFFERENTIATED AND PRIMARY CELLS WITHOUT THE NEED FOR POST-THAW WASHING AND CENTRIFUGATION STEPS, each of which is incorporated by reference in its entirety herein.

BACKGROUND OF THE INVENTION

Field of the Invention

The present invention relates to a process for freezing and thawing of living and sensitive cells, particularly primary and differentiated cells, and particularly an improved freezing method for subsequent cell thawing and direct plating or suspension use that avoids the need of removal of a cryoprotective agent, like DMSO. This is a rapid and user-friendly method, which is very useful for using cryopreserved living cells as cell-based assays for cell biological applications.

Description of Related Art

With limited supply of available tissue or cells, cryopreservation remains the best method for long-term storage of cells, allowing a permanent and sufficient cell supply and greater flexible scheduling. A number of freezing solutions and process are known in the art of cryopreservation for long-term storage of living cells in either liquid nitrogen LN, −196° C.) or vapor-phase nitrogen (−189° C.). The cryoprotectants, including permeating and nonpermeating types, are essential components of freezing medium, since they prevent the formation of both intra- and extracellular ice crystals and hence cell freezing injury or cell death. Classically, dimethyl sulfoxide (DMSO), the most widely used cryoprotectant, is usually used at a final concentration of 10 to 12% (v/v) combined with a cold carrier solution (such as a standard serum-containing medium, or improved preservative solution like University of Wisconsin solution (UW) or Hypothermosol (HTS)). Moreover, it has been confirmed that the use of the optimized carrier solution allows a decrease in the DMSO level within the freezing solution (Stephenne et al., (2010). Hepatocyte cryopreservation: is it time to change the strategy? *World J Gastroenterol.* 16(1): 1-14).

All cryoprotectants are likely to have toxic effects on the cells, especially permeating cryoprotectants which typically have low molecular weight. DMSO, an industry-standard cryoprotectant, has been demonstrated to be toxic above to 4° C. when its concentration is up to 2% (Loretz et al., (1989). Optimization of cryopreservation procedures for rat and human hepatocytes. Xenobiotica 19:489-498; Baust et al., (2002). Modulation of the cryopreservation cap: elevated survival with reduced dimethyl sulfoxide concentration. Cryobiology 45(2):97-108; Stephenne et al., 2010). DMSO has been determined to be non-toxic and effective during long-term LN storage and to be the less toxic among the permeable cryoprotectants. The degree of cryoprotectant toxicity to cells is proportional to its concentration in the cell solution and temperature during freezing and thawing process. Therefore, it is a universally-accepted requirement and practice that the cryopreserved cells are thawed quickly (<2 min.) at 37° C. and diluted in pre-warmed thawing medium, followed rapidly by centrifugation and removal of cryoprotectant-containing supernatant in order to minimize the toxic effects. This post-thaw wash step is vital for successful use of cryopreserved primary and differentiated cells, because they are extremely fragile upon recovery from cryopreservation. It requires close attention to protocols which vary by cell type and if not correctly performed, will cause either damage to the cells or loss of some cell population (decrease in cell numbers or loss of viability).

This is the main reason that a standard thawing procedure is already established in the art as beneficial for the recovery of the cryopreserved cells. Basically, industry-standard protocols exist for thawing conditions and include thawing cells in a 37° C. water bath, dilution of thawed cells with thawing medium, and centrifugation to remove cryoprotectant from cell culture. Removal of cryoprotectant from thawed cell suspension, such as DMSO via a post-thaw wash spin is required particularly for sensitive cells, including cryopreserved primary and differentiated cells, like human hepatocytes, as well as differentiated hepatocyte like cells, and also liver progenitor cells. For cell-based assays, the amount of DMSO is typically less than 2%, since higher concentrations of DMSO could be harmful to cells, for example, dissolving cell membranes.

The standard process for post-thaw removal of cryoprotectant in use for over a decade, consists of two main procedures: (i) Thaw, spin, and resuspend: the frozen cells are thawed in pre-warmed medium, then centrifuged at room temperature, followed by removal of DMSO-containing supernatant, and then re-suspended in a DMSO-free medium; (ii) Count, plate, or incubate: the viability, yield and concentration of resuspended cells are determined. The recovered cells can then be used either in suspension or plated assays after correct density dilution and plating.

It is vital and critical that, following thawing, sensitive cells maintain their viability and recover quickly from the stresses of cryopreservation and thawing. However, this classical cell thawing and recovering process is time-consuming and costly, with higher risk of contamination due to additional handling and resuspension of the thawed cells, and high probability of loss of cell population due to die-off, as well as considerable variation in number of cells recovered due to inter-operator variations. Hence, either a highly skilled operator or specific training for non-specialist operators is required to ensure quality and consistency in the process. In addition, there is a limited throughput with this classical thawing method since no more than two vials can be properly thawed simultaneously by an operator.

SUMMARY OF THE INVENTION

The present invention is broadly concerned with a simple and rapid method for eliminating the necessity of post-thaw wash, spin, and frequent practice of performing a cell count, and thus to reduce all related risks, inconvenience and inaccuracy, the present invention provides an optimized freezing method that allows direct cell thawing and suspension or plated assay.

In one aspect, methods for preparing cells for cryopreservation are provided. The methods comprise providing a concentrated cell suspension comprising a first amount of cells either in pellets or pre-dispersed in a suspension medium; providing a freezing solution comprising a cryoprotectant dispersed in medium or carrier solution; mixing the concentrated cell suspension with the freezing solution to yield a cryopreservation mixture; and subjecting the cryopreservation mixture to cryopreservation to yield a concentrated composition of cryopreserved cells.

Concentrated compositions of cryopreserved cells are also disclosed. The concentrated compositions of cryopreserved cells are prepared by providing a concentrated cell suspension comprising a first amount of cells dispersed in a suspension medium; providing a freezing solution comprising a cryoprotectant dispersed in medium or carrier solution; mixing the concentrated cell suspension with the freezing solution to yield a cryopreservation mixture; and subjecting the cryopreservation mixture to cryopreservation to yield a concentrated composition of cryopreserved cells.

Also described herein are methods for thawing and recovery of cryopreserved cells. The methods comprise a concentrated composition of cryopreserved cells prepared according to the inventive methods. The concentrated composition of cryopreserved cells is thawed to yield a thawed composition of cells, wherein the thawed composition of cells comprises thawed cells and cryoprotectant dispersed in a medium, followed by directly plating the thawed composition of cells or directly suspending the thawed composition of cells in a suspension assay, without removal of the cryoprotectant.

A no-spin cell product is also described herein. In other words, the cell product is characterized by being able to be used directly for plating and/or suspension without washing, sedimentation, decantation, centrifugation, and/or counting when the cell product is thawed. The no-spin cell product consists of a concentrated composition of cryopreserved cells. The concentrated composition of cryopreserved cells comprises a first amount of cells and a freezing solution comprising a cryoprotectant dispersed in medium or carrier solution. The cells are dispersed in the freezing solution.

DETAILED DESCRIPTION OF PREFERRED EMBODIMENTS

The present invention is concerned with methods/processes for preparing cells for cryopreservation and thawing and recovery of cryopreserved cells, as well as resulting "no-spin" cell products. The inventive freezing and thawing of sensitive, cryopreserved living cells described herein advantageously avoids the need for post-thaw washing and removal of harmful cryoprotective agents prior the use of thawed cells in related applications. The terms "freezing," "frozen," and the like are used herein synonymously with cryopreserving or cryopreserved, which more specifically refer to controlled cooling of tissues and cells to low sub-zero temperatures such that any biological activity is effectively stopped to preserve the cells or tissues at these sub-zero temperatures, and is not intended to refer to the generic concept of freezing that encompasses unprotected or uncontrolled freezing.

The objectives of the invention are achieved by an innovative concept of freezing the same number of cells as is typically used in the standard method but in a reduced fluid volume, consequently, cell concentration is increased but the amount of cryoprotective agent is decreased in relation to the cell suspension to be frozen. In this case, if the frozen cells are then thawed in a same volume of thawing medium as is typically used in a standard method, the concentration of cryoprotectant is diluted significantly to able to achieve a non-toxic concentration. The method eliminates the step of spin-down washing for removal of cryoprotectant from the thawed cell suspension. In addition, the diluted cell suspension can be adjusted to a desired density and used directly for cell plating or suspension by the end-users without the requirement of post-thaw, spin-down washing and routine cell count steps.

The innovative process results in "no-spin" cell products that can be used in various cell culturing or plating methods, where the term "no-spin," as used herein, refers to a characteristic or property of the resulting cell products that permits them to be used directly for plating and/or suspension without washing, sedimentation, decantation, centrifugation, and/or counting after thawing.

Therefore, two main advantages generated in this innovation are: (i) to provide an effective freezing and thawing process for minimizing toxic effects of cryoprotectants attributed to cell quality and related applications, without requirement of post-thaw spin-down washing; and (ii) to provide a simple, user-friendly and higher throughput method for the use of frozen and sensitive cells without the requirement of frequent practice of performing a cell count.

In more detail, a method of preparing cells for cryopreservation is provided. The method comprises providing a concentrated cell suspension that comprises (consists essentially or even consists of) cells dispersed in medium. The concentrated cell suspension can be prepared by mixing a target amount of cells (first amount) in a suspension medium. As used herein, a "concentrated cell suspension" is defined as a cell suspension in which the target amount of cells corresponds to the standard or customary cell amount or range generally accepted in the industry for the particular cell type, but which comprises a reduced volume of suspending medium. In one more embodiments, the suspending medium is reduced by at least about ½ (50%) of the standard volume or volume range in the industry for the particular cell type and/or medium. As used herein a "standard" amount or volume is a value that is recommended and/or established for standard operating procedures in the industry for conventional applications of the given cell or medium type. Such values are known in the art. In one or more embodiments, the concentrated cell suspension will comprise from about 2 million cells/mL to about 200 million cells/mL. The invention is suitable for use with a variety of living cells and cryoprotectant-sensitive cells, including primary and differentiated cells, such as hepatocytes, cell lines (HepaRG®), stem cells, stem cells, induced pluripotent stem cells, reprogramming cells, renal cells, non-parenchymal cells, pre-adipocytes, skin cells, blood cells, and the like. The cells can be isolated from animal and/or human tissues or trypsinized from primary or differentiated cell cultures. Any suitable media can be used for the cell suspension medium, including standard complete culture medium, with or without supplemented, non-penetrating cryoprotectants, or improved freezing carrier solutions, such as Viaspan, HTS, Prolong, and the like.

The method further comprises providing a corresponding volume of freezing solution. The freezing solution comprises (consists essentially or even consists of) an effective concentration of cryoprotectant in a suitable solvent system (carrier solution or medium). As used herein, the "corresponding volume" means an amount that corresponds to the total volume of the prepared concentrated cell suspension. In general, there will be a 1:1 correspondence of the concentrated cell suspension and freezing solution volumes. For example, if the total volume of the concentrated cell suspension is 0.5 mL, then the corresponding volume of freezing solution would also be 0.5 mL, in this case, the volume ratio between the concentrated cell suspension and freezing solution is 1:1. However, the volume ratio can be varied in two senses, at range of 0.1 to 1.9, or 1.9 to 0.1, for example. The freezing solution comprises a standard and complete culture medium or an improved freezing carrier solution supplemented with a penetrating cryoprotectant. Exemplary cryoprotectants include, without limitation ethylene glycol, propylene glycol, dimethyl sulfoxide (DMSO), fetal bovine serum (FBS), propanediol, glycerol, as well as mixtures of the foregoing. DMSO is particularly preferred for cryopreservation of hepatocytes. Other suitable freezing solutions include commercially-available cryoprotectant-supplemented media, such as FrostaLife™, CryoStor®, Hepatocyte Storage Medium, as well any standard culture medium like William's E, L15, DMEM, HCM, Chees medium supplemented with appropriate amount of DMSO, and the like. The "effective concentration" of the cryoprotectant in the freezing solution will depend upon the recommended or established amounts for the particular cryoprotectant. For example in the case of DMSO, the effective concentration of DMSO can range from about 5% to about 20% (v/v), with from about 10% to about 12% being particularly preferred in some aspects of the invention.

In the method, a cryopreservation mixture is prepared by mixing the concentrated cell suspension with the prepared freezing solution. Thus, the cryopreservation mixture comprises (consists essentially or even consists of) the concentrated cell suspension and the prepared freezing solution. In general, the total volume of cryopreservation mixture will range from about 0.1 mL to about 200 mL. The cryopreservation mixture is then frozen according to the desired cryopreservation protocol.

In one or more embodiments, the resulting cryopreservation mixture is distributed into aliquots in a container suitable for cryopreservation. In general, no other additives are added or included in the container. Exemplary containers for cryopreservation include straws, ampules, cryovials, cryotubes, or freezing bags, generally ranging from about 1 mL to 250 mL. Each container is then transferred to a freezing device, such as Mr. Frosty slow-freeze device for cooling and freezing of the cryopreservation composition under controlled conditions (time, temperature, rate, etc.). In general, the cryopreservation mixture, containing the cells is frozen according to a standard stepwise freezing method or a computer-controlled freezing method. The resulting cryopreserved composition is then stored under nitrogen, or in an ultra-low freezer (−70° C. or below), or in Freon, etc. to maintain the cryopreserved state. For example, the freezing process and cryopreservation storage can be carried out with either a standard stepwise procedure (−20° C., then −80° C., then storage in either vapor-phase nitrogen (−189° C.) or liquid nitrogen (−196° C.), or a semi-controlled procedure using a Mr. Frosty or other freezing device (−80° C., then storage in liquid nitrogen (−189 to −196° C.) or other computer-controlled, automated freezing procedure. It will be appreciated that the foregoing procedure yields a concentrated composition of cryopreserved cells that comprises (consists essentially or even consists of) the concentrated cell suspension and the prepared freezing solution mixture in a cryopreserved state. In other words, the resulting concentrated composition of cryopreserved cells is a no-spin cell product.

Also described herein, are methods of thawing and recovering cryopreserved cells. In the method, a concentrated composition of cryopreserved cells is provided. In general, the concentrated composition of cryopreserved cells will have a cell concentration that is at least two-times the standard cell concentration, whereas the relative amount of cryoprotectant is decreased with respect to the total cell amount. The method comprises thawing the concentrated composition of cryopreserved cells to yield a thawed and diluted composition of cells that comprises the cells and cryoprotectant. In one or more embodiments, the thawing comprises placing the container of the concentrated composition of cryopreserved cells at least partially submerged in a warming water bath or any warming system (e.g., at 37° C.) until at least partially thawed (i.e., until the frozen composition is loosened from the container walls and ice crystals are substantially thawed. The at least partially-thawed concentrated composition of cells is then diluted with prewarmed thawing and plating medium to achieve a second (diluted) amount of cells. The at least partially-thawed concentrated composition of cells can be mixed with the prewarmed thawing and plating medium by adding the medium to the cryopreservation container, or by transferring the at least partially-thawed concentrated composition of cells to a separate (second) container which already contains the medium or to which the medium is subsequently added, to ultimately yield a diluted composition of cells comprising a second amount of cells for direct plating or suspension. In one or more embodiments, thawing comprises adding prewarmed thawing and plating medium into the cryopreservation container with the concentrated composition of cryopreserved cells to simultaneously thaw and dilute the cell composition, to ultimately yield a diluted composition of cells comprising a second amount of cells for direct plating or suspension. Exemplary thawing and plating medium include complete growth or seeding media, any standard assay media (e.g., L15, WEM, RPMI, DMEM, Chees Medium), or any improved thawing media (e.g., UW, HTS, HCM), and the like, as well as mixtures thereof. In one or more embodiments, the concentrated composition of cryopreserved cells can be thawed directly using suspension assay buffer, such as phenol-red free PBS, HBSS, MEM, WEM, and the like. The thawed composition can be further diluted to adjust the cell concentration to the desired target amount or range (third amount of cells) for subsequent plating and/or suspension, if desired.

Advantageously, the resulting thawed and diluted composition of cells can be used directly for plating and/or suspension without subjecting the thawed composition of cells to spin-down (centrifugation), washing, and/or removal of the cryoprotectant media. Accordingly, unlike existing approaches, the resulting thawed compositions of cells used for plating and/or assaying will comprise amounts of cryoprotectant. Although the relative volume of the cryoprotectant will have been diluted, it will be appreciated that the cryoprotectant will still be present at levels significantly greater than mere residual amounts that might unintentionally remain in conventional cell processing. Thus, in one more embodiments, the resulting thawed and diluted composition of cells is plated as a cell monolayer onto a culture plate. In one or more embodiments, the thawed composition of cells is suspended in suspension assay media for dilution, and used directly in the desired assay system. In other words, the resulting thawed cells perform like cells cryopreserved and thawed using conventional techniques. For example, inventive prepared cells are characterized by having one or more biomarkers that are not significantly different from conventionally prepared cells: post-thaw viability, morphology, plateability, cell growth and differentiation, basal metabolic activity, induced metabolic activity, drug clearance, drug transporters activities, confluence, and the like. As used herein, a biomarker is not "significantly" different if visual inspection is unable to ascertain perceivable differences affecting the performance of the cells, or if the different value for a biomarker remains within accepted ranges (standardized specifications) expected for conventionally-processed cells. A used herein "conventionally" processed or prepared cells refers to cells processed using the techniques described herein as conventional (e.g., cryopreserved at a more diluted cell concentration and with higher relative concentrations of cryoprotectant, and requiring a post-thaw removal of cryoprotectant, such as by centrifugation and washing).

In view of the foregoing, a specific example implementing the inventive techniques is as follows. The concentrated cell suspension in freezing solution is prepared for cryopreservation using final concentrations of 10% DMSO and 10 million cells/vial. The target of 0.8 million cells/mL is used for the final concentration in the thawing/seeding medium for cell plating, with 1% DMSO as a maximum tolerated percentage in the cell plating/incubation/thawing medium. Thus, if the 10 million cells are concentrated into 0.25 mL (1 vial), such that the concentration corresponds to 20 million cells/mL, and then, a 0.25 mL freezing solution with 20% DMSO (1 vial) is added into the concentrated cells, thus, the final volume of cell mixture is 0.5 mL containing 10 million cells and a final of concentration of 10% DMSO. Thus, in using the direct no-spin thawing and plating technique, the 0.5 mL of frozen cells is thawed into a volume of 12 mL of thawing/plating medium in order to get 0.8 million cells/mL, without the need of cell washing and further concentrating step. As a result of the dilution of 0.5 mL cell mixture into 12 mL medium (25-fold dilution), the resulting DMSO concentration is only about 0.4% (below 1%). As such, the cells can be used directly without washing, centrifugation, etc. and without the risk of DMSO toxicity.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

"No Spin" Processing of Cryopreserved and Thawed Hepatocyte Cell Line

Figure 1:
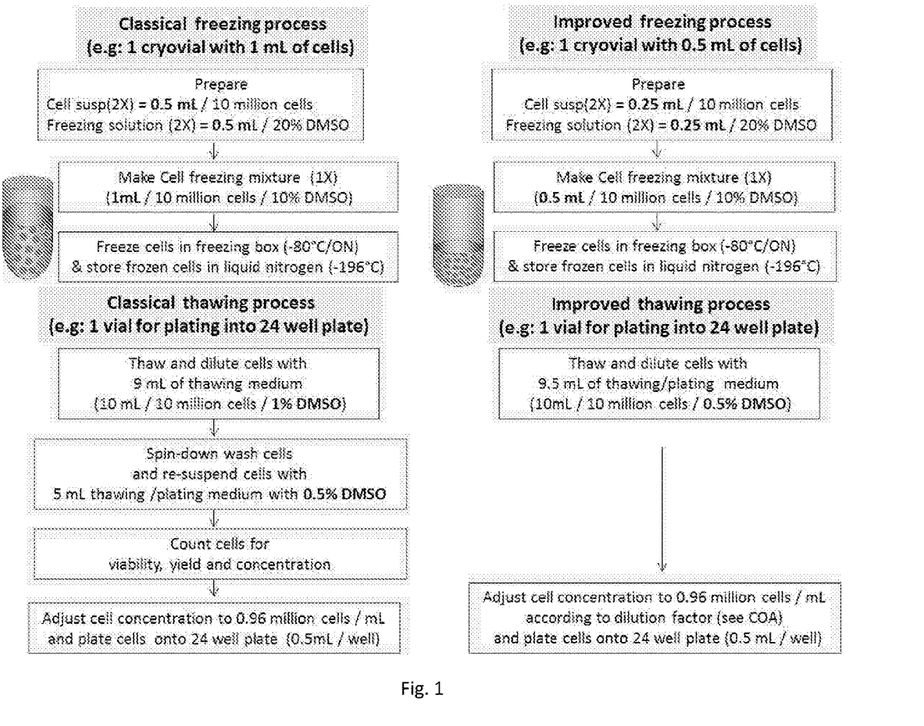
FIG. 1 illustrates a comparison of a conventional cryopreservation and thawing process as compared to the inventive no-spin cryopreservation and thawing process.

HepaRG® cells (human hepatoma cell line deposit no. 1-2652, filed on 5 Apr. 2001 at the Collection Nationale de Cultures de Microorganismes, Institut Pasteur, 25 rue du Docteur Roux, F-75724 Paris Cedex 15, U.S. Pat. No. 7,456,018, incorporated by reference herein) are terminally differentiated hepatic cells derived from a human hepatic progenitor cell line that retains many characteristics of primary human hepatocytes. Cryopreserved and differentiated HepaRG® cells (Biopredic, Inc.) are now widely used for many cell-based applications, consequently, methods used for the cell freezing, thawing and post-thaw applications should be simple and user-friendly. This example of freezing and thawing process as illustrated with a schematized protocol compares both classical and improved no-spin methods as shown in FIG. 1.

A. Trypsinizing & Freezing Process

Step 1. Trypsinizing and Generating of Cell Suspension Prior Cell Freezing

HepaRG® cells, as cell source to be cryopreserved, were cultured and differentiated on a monolayer in Cell Factory (CF, 2500 cm$^2$) with complete differentiating medium until terminally differentiated (Antherieu at al., (2010). Stable expression, activity, and inducibility of cytochromes P450 in differentiated HepaRG® cells. Drug Metab Dispos. 38(3): 516-25). Those cells were then harvested by a standard trypsinization procedure to detach adherent cells from the culture surface of CF, followed by washing, pelleting and re-suspending procedure. The volume of cell suspension obtained from 2 CF was measured and was equal to 18 mL in total. The cell viability, yield and concentration were then determined by using a standard Trypan blue staining assay.

Step 2: Determining Cell Viability and Yield Using Trypan Blue Staining

Even when differentiated HepaRG® cell culture are dissociated by trypsin and homogenized by pipetting and filtered, there are still many multicellular clusters or cell aggregates present in a HepaRG® cell suspension, so cell counting is a very critical step for HepaRG® cells in this method. Usually, the number of cells in 6 lines/columns in Nageotte Chamber should be counted by at least two skilled operators to ensure the accuracy of a cell count. Cell viability, yield and cell concentration were determined by Trypan blue staining. 10-fold serial dilutions were made by first adding 100 µl of a well homogenized cell suspension into one tube containing 900 µL of Trypan blue solution (0.05% in D-PBS 1×, Sigma), then followed by a second dilution, in which, 100 µL of 10-fold diluted suspension was added into second tube with 900 µL Trypan blue. The diluted and well-mixed cell suspension was introduced into a counting chamber. Both living and dead cells were counted under microscope, living cells exclude the dye while dead cells take it up and appear blue.

The cell viability (%) was determined with average values according to the following formula:

Number of viable cells/(Number of viable cells+ Number of dead cells)×100=% of viability Result: cell viability=94%

The cell concentration (million cells/mL) was calculated with average values according to the following formula:

Number of viable cells per row×100 (dilution factor)×800 (Nageotte factor)=Million cell/mL Result: cell concentration=28 million cells/mL The total cell number (million cells/18 mL of cell suspension) was calculated according to the following formula:

Cell concentration in million cells/mL×Total volume of cell suspension=total cell number in suspension Result: cell yield=504 million cells in 18 mL of cell suspension Step 3: Freezing HepaRG® cells: Classical versus new method Once the cell concentration (28 million cells/mL) and cell number (total of 504 million cells in 18 mL) were evaluated in Step 2, the cell suspension was divided into two equal parts (2×9 mL), each part with 252 million cells in 9 mL suspension. These two suspensions were further prepared as cell sources for producing two lots of cryopreserved HepaRG® cells according to the following two methods and related specification in order to evaluate the two tested post-thaw procedures:

(i) A standard lot (HPR116-S) was produced with classical freezing method; consequently, a spin down for cell washing during the post-thaw procedure was required for removing DMSO from a thawed cell suspension before cell plating.

The target specifications for classical freezing method:
2-fold concentrated cell suspension is 25 million cells/mL
2-fold concentrated freezing medium is supplemented with 20% DMSO (v/v)
Final cell concentration in mixture of cells with freezing medium is 12.5 million cells/mL
Final DMSO concentration in mixture of cells with freezing medium is 10% (v/v)
Final distributed/aliquoted cryovial is 12.5 million cells in 1 mL per cryovial (ii) A new lot (HPR116-NS, where NS stands for "no spin") was produced using the improved freezing method; therefore a spin-down for washing cells during the post-thaw procedure is not required for removing DMSO from that thawed cell suspension before cell plating.

The target specifications according to the new concept for improved freezing method:
2-fold concentrated cell suspension is 50 million cells/mL
2-fold concentrated freezing medium is supplemented with 20% DMSO (v/v)
Final cell concentration in mixture of cells with freezing medium is 25 million cells/mL
Final DMSO concentration in mixture of cells with freezing medium is 10% (v/v)
Final distributed/aliquoted cryovial is 12.5 million cells in 0.5 mL per cryovial However, two common protocols were established for producing two lots: with an equal number of cells (12.5 million viable cells) in each vial and the same concentration of DMSO (10%) in each cell suspension, while the suspension volume per vial in the new lot was just half of suspension volume per vial in the standard lot, as a result, double concentration of cells (25 million cells/mL) was obtained in new lot.

Based on the determined cell concentration (28 million cells/mL), the 2-fold concentrated cell suspensions were adjusted according to the above specifications of two methods.

Freezing HepaRG® Cells with Classical Method

For the first part of the cell suspension (9 mL) used in the classical freezing method, an additional suspension medium (1.08 mL) was added to bring cell suspension to the desired 2-fold concentrated cell suspension (25 million cells/mL). Then, an equal volume (10.08 mL) of two-fold concentration of complete cryopreservation medium containing 20% of DMSO was added slowly into the 2× cell suspension within 4 minutes, thus, ⅕ volume of DMSO-containing medium was added into the 2× cell suspension each minute. At the end of 4 min, 1 mL of the cell mixture was distributed into each of 20 pre-labelled cryovials according to the specification. The cell-filled cryovials were then transferred into a precooled "Mr Frosty" freezing device (18 vials/freezing device). As soon as the 20 minutes of pre-freeze equilibration period at 4° C. was completed, the "Mr. Frosty" freezing container filled with cryovials was placed into a −80° C. freezer for semi-controlled cooling. After overnight storage at −80° C., the 20 cryovials were removed out from the freezing container and immediately placed into a liquid nitrogen tank for long-term storage.

Freezing HepaRG® cells with Improved No-Spin (NS) Method

For the second part of the cell suspension (9 mL) used in new freezing method, the volume of cell suspension was reduced from 9 mL to 5.04 mL to bring the cell suspension to the desired 2-fold concentrated cell suspension (50 million cells/mL), according to the concept of the invention. For that, the cells in suspension were first pelleted by a centrifugation at 500 g at 4° C. for 3 minutes after adding 5 volumes of complete proliferating culture medium (45 mL). The pelleted cells were re-suspended in a final of 5.04 mL of suspension medium; consequently the cells were concentrated to 50 million cells/mL. Then, an equal volume (5.04 mL) of two-fold concentrated complete cryopreservation medium containing 20% of DMSO was added slowly into 2× cell suspension within 4 minutes, thus, ⅕ volume of DMSO-containing medium was added into the 2× cell suspension each minute. At the end of the mixing step, 0.5 mL of cell mixture was distributed into each of 20 pre-labelled cryovials according to the specification. The cell-filled cryovials were then transferred into a precooled "Mr. Frosty" freezing device (18 vials/freezing device). As soon as the 20 minutes of pre-freeze equilibration period at 4° C. was completed, the "Mr. Frosty" freezing container filled with cryovials was placed into a −80° C. freezer for semi-controlled cooling. After overnight storage at −80° C., the 20 cryovials were removed from the freezing container and immediately placed into a liquid nitrogen tank for long-term storage.

B. Thawing & Seeding Process

The cryopreserved HepaRG® cells in two lots (HPR116-S and HPR116-NS) were thawed and seeded using two different thawing and seeding procedures:

Thawing and Seeding HepaRG® Cells Using a Classical Method

Step 1: Thawing & Recovering HepaRG® Cells Using Classical Method

In general, cryopreserved cells, particularly from sensitive or fragilized cells, including physical stressed cells, osmotically stressed cells, enzymatically isolated primary cells and differentiated cells, should be thawed as quickly as possible to prevent formation of ice crystals that can affect cell viability. So it is recommended to thaw no more than two vials per operator at one time in classical thawing method. 1 vial of the lot HRP116-S (produced by standard freezing method) was removed from a liquid nitrogen container and immediately placed into a 37° C. water bath without submerging the vial completely. As soon as the cells were "semi"-thawed (~2 minutes) with just a small crystal of ice remaining, the vial was removed from the water bath and the outside of the vial was wiped with 70% ethyl alcohol and then placed under a laminar flow hood before opening.

The 1-mL thawed cell suspension containing 10% DMSO was then gently transferred from the vial into a tube with 9 mL of pre-warmed Thawing and Plating Medium containing 0.5% DMSO (Biopredic), and the content of the vial was rinsed once with the same medium (1 mL/vial) and transferred again into the tube. The recovered cells were then spun down for three minutes at 500×g centrifugation, followed by discarding the supernatant containing DMSO. The pelleted cells were re-suspended with 5 mL of the same medium with 0.5% DMSO (a sufficiently low percentage that doesn't cause any toxicity to cells). The resuspended cell suspension was kept on wet-ice for the next step.

Step 2: Determining Thawed Cell Viability and Yield Using Trypan Blue Staining

As described above, there can still be many multicellular clusters or cell aggregates in the HepaRG® cell suspension before freezing, consequently they are also included in the thawed and resuspended cell solution. So, again HepaRG® cell counting, like some other cell types which easily form aggregates, is a very important step for making an appropriate seeding density before cell plating. Cell viability, yield and cell concentration are determined by Trypan blue staining. The number of cells present in six columns/row of Nageotte Chamber was counted under microscopy for an accurate cell count.

A 10-fold dilution was made by adding 100 μL of well homogenized cell suspension into one tube containing 900 μL of Trypan blue solution (0.05% in D-PBS 1×, Sigma). The diluted and well mixed cell suspension was introduced into a counting chamber. Both living and dead cells were counted under microscope, living cells exclude the dye while dead cells take it up and appear blue.

The cell viability (%) was determined with average values according to the formula in the box below:

(Number of viable cells/(Number of viable cells+ Number of dead cells))×100=% of viability The cell concentration (million cells/mL) was calculated with average values according to the formula in the box below:

Number of viable cells per row×10 (dilution factor)× 800 (Nageotte factor)=M cell/mL The total cell number (million cells/5 mL of cell suspension) was calculated according to the formula in the box below:

Cell concentration in million cells/mL×Total volume of cell suspension=total cell number in suspension Step 3: Seeding Thawed Cells onto a Collagen Coated 24 Well Plate.

The Target Specification for the Seeding as Follows:
Required number of cells
For each 24 MW plate: ~11.5 million cells
For each 96 MW plate: ~6.9 million cells
So, a vial containing ~10.0 million viable cells will be sufficient for ~21 wells of a 24 MW plate (0.48 million cells/well), or for a 96 MW plate and ~43 additional wells (0.072 million cells/well)
The recommended cell density for plating on 24 well plate: 0.96 million cells/mL
The recommended cell density for plating on 96 well plate: 0.72 million cells/mL
So for the lot HPR116-S, a final volume of 10.93 mL of cell suspension was made by adding additional 5.93 mL of thawing and plating medium before plating the cells. Next, 0.5 mL of the cell suspension was dispensed into each well of 24-well plate; the filled plate was then agitated horizontally back and forth and right-and-left to form a homogeneous cell monolayer. Then the plate was placed into a 5% $CO_2$ incubator at 37° C.

Thawing and Seeding HepaRG® cells Using an Improved Method

Step 1: Thawing and Recovering HepaRG® Cells

In general, frozen cells are more fragile or stressed cells. Particularly, the cryopreserved cells from freshly isolated primary cells and differentiated cells should be thawed as quickly as possible to prevent or reduce the potential harmful risks of cell thawing: (i) to prevent the formation of ice crystals during the thawing that can affect cell viability, (ii) to reduce cryoprotectant toxicity that is resulted from high concentration of cryoprotectant during warm temperature cell thawing, such as >2% of DMSO at 37° C.

One vial of the lot HRP116-NS (produced by new freezing method) was removed from a liquid nitrogen container and immediately placed into a 37° C. water bath without submerging the vial completely. As soon as the cells were "semi"-thawed (~1 minute) with just a small crystal of ice remaining, the vial was removed from the water bath and the outside of the vial was wiped with 70% ethyl alcohol and then placed under a laminar flow hood before opening.

The 0.5-mL thawed cell suspension containing 10% DMSO was then gently transferred from the vial into a tube with 9.5 mL of pre-warmed thawing and plating medium, and the vial was rinsed once with 1 mL of the same medium to capture any vial contents attached to its walls and was transferred again into the tube. Finally, the amount of DMSO was diluted twenty-fold in Thawing and Plating Medium; as a result, the 10% of DMSO was reduced to a level of 0.5%, which is a concentration bestowing a margin of safety, and does not affect the cell attachment efficiency after cell plating.

Meanwhile, the resulting cell concentration was about 1 million cells/mL, 10 million cells in 10 mL of cell suspension; in addition, the cell viability, yield and concentration of the thawed cells from the lot HPR116-NS were checked. The viability was 93%, and yield was 10.8 million viable cells/vial, so the concentration was 1.08 million viable cells/mL. The thawed and diluted cell suspension was ready to be used for experiments without the end-user requirements of post-thaw washing, centrifugation, and counting.

Step 2: Seeding Thawed HepaRG® onto a Collagen Coated 24-well plate

The Target Specification for the Seeding as Follows:
Required number of cells
For each 24 MW plate you will need ~11.5 million cells
For each 96 MW plate you will need ~6.9 million cells
So, a vial containing ~10.0 million viable cells will be sufficient for ~21 wells of a 24 well plate (0.48 million cells/well), or for a 96 well plate and ~43 additional wells (0.072 million cells/well)

The recommended cell density for plating on 24 well plate: 0.96 million cells/mL The recommended cell density for plating on 96 well plate: 0.72 million cells/mL Total volume=concentration (million cells/mL)×dilution factor* (1.05) for 24 well plate

*The dilution factor will be indicated in the end-user Certificate Of Analysis for diluting cells but without requiring the steps of post-thaw washing and cell counting.

For the lot HPR116-NS, a final cell suspension volume of 11.34 mL was made by adding 1.34 mL of thawing and plating medium before the cells were plated. Next, 0.5 mL of the cell suspension was dispensed into each well of a 24-well plate, and the filled plate was agitated horizontally back and forth and right-to-left in order to form a homogeneous cell monolayer. Then the plate was placed into a 5% $CO_2$ incubator at 37° C.

C-Comparison Results Obtained in Thawing and Plating Process:

1. Comparison of Thawed Cell Viability and Yield: HPR116-S vs HPR116-NS

The cells frozen by a classic method (HPR116-S) were thawed in thawing and seeding medium, washed by centrifugation and resuspended according to the User Instructions which have been applied to these cells for approximately three years; while the cells frozen by an improved method (HPR116-NS) were thawed in about 10× volume of thawing and plating medium. The table below contains a comparison of the thawed cell viability and yield between HPR116-S and HPR116-NS:

| Cell viability & yield after thawing | Classical freezing and thawing method (HPR116-S) | Improved freezing and thawing method (HPR116-NS) |
|---|---|---|
| Post-thaw viability (% viable cells) | 93% | 93% |
| Post-thaw yield (Million cells/vial) | 10.5 | 10.8 |

Observation: Similar yields and viabilities were obtained from both HPR116-S and HPR116-NS, prepared with either classic or improved method. The data were comparable and acceptable.

2. Cell Morphological Observation: HPR116-S vs HPR116-NS

Figure 2:
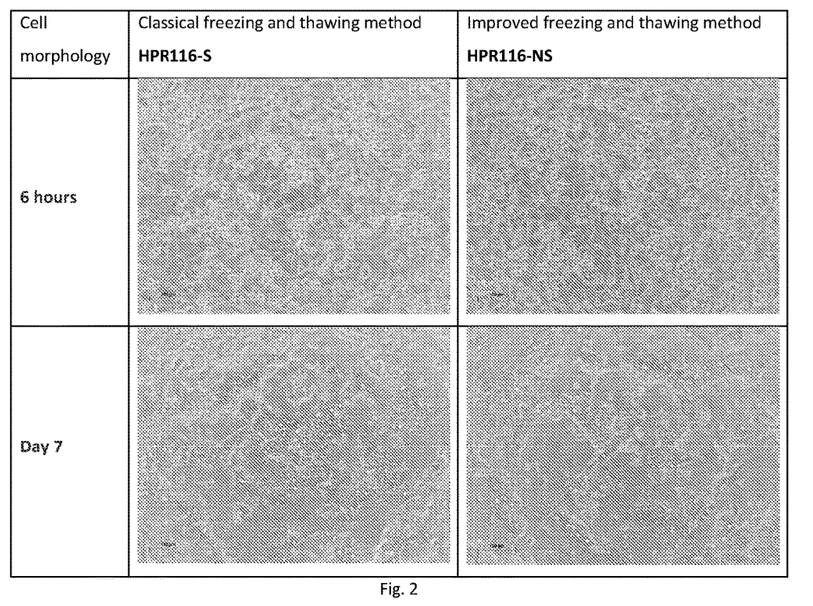
FIG. 2 shows images of cell monolayers from standard (HPR116-S) and no-spin (HPR116-NS) processed HepaRG® cells from Example 1.

After thawing and plating, cell cultures were maintained in differentiation medium for one week, cell morphologies were also observed at different time points, as illustrated in FIG. 2. Observation: Six hours after plating, a similar cell attachment efficacy was observed on HPR116-NS cells prepared from direct thawing and plating, as compared to the HPR116-S cells from classic thawing and plating procedure. The cell cultures from the two types of cell preparations reached 100% confluence six hours post seeding. Seven days after plating and culture, hepatocyte-like cell clusters were formed in both HPR116-S and HPR116-NS cultures and their morphology was comparable.

3. Comparison of Metabolic Activity and Inducibility: HPR116-S vs HPR116-NS

The table below contains a comparison of the functional activity of thawed cells from classic cryopreserved and differentiated HPR116-S, and differentiated and cryopreserved HPR116-NS cells. In summary, suspensions of both classic HPR116-S and HPR116-NS cells were adjusted for proper cell concentration and used in the following analyses which are commonly used in the industry to assess cell health and function. The metabolic activities were measured both in suspension as basal metabolic activity (day 0) and on cell monolayer at day 7, as well as the inducibility of cytochrome P450 by some reference inducers. The use of either a suspension or plated procedure was consistent between the classic HPR116-S cells and the improved HPR116-NS.

(i) Basal Metabolic Activities

The basal activity data are shown in the tables below:

| Enzymatic activities were expressed as nmol/h/$10^6$ cells | | | |
|---|---|---|---|
| Cytochrome P450 activity on cell suspension (Day 0) | | Classic process HPR116-S | Improved process HPR116-NS |
| phenacetin-O-deethylase activity | CYP1A2 | 0.5 | 0.5 |
| midazolam 1' hydroxylase activity | CYP3A4 | 2.5 | 2.4 |
| bupropion hydroxylase activity | CYP2B6 | 0.4 | 0.4 |

| Enzymatic activities were expressed as nmol/h/mg of proteins | | | |
|---|---|---|---|
| Cytochrome P450 activity on cell monolayer (Day 7) | | HPR116-S | HPR116-NS |
| phenacetin-O-deethylase activity | CYP1A2 | 1.2 | 1.3 |
| midazolam 1' hydroxylase activity | CYP3A4 | 9.5 | 7.5 |
| bupropion hydroxylase activity | CYP2B6 | 1.5 | 1.1 |

Observation: the results for basal metabolic activities of CYP1A2, CYP3A4 and CYP2B6 were similar between the cryopreserved HPR116-S and HPR116-NS cells produced by using either the classical or the improved process.

(ii) Induced Metabolic Activities

| Inducibility of CYP1A2 activity (phenacetin-O-deethylase activity) | Vmax value (nmol/h/mg proteins) | | |
|---|---|---|---|
| Induction ± Omeprazole 50 µM | Un-induced | Induced | Fold induction |
| HPR116-S | 0.5 | 1.6 | 3.2 |
| HPR116-NS | 0.5 | 1.3 | 2.6 |

| Inducibility of CYP3A4 activity (midazolam 1' hydroxylase activity) | Vmax value (nmol/h/mg proteins) | | |
|---|---|---|---|
| Induction ± Rifampicin 10 µM | Un-induced | Induced | Fold induction |
| HPR116-S | 1.0 | 6.7 | 6.7 |
| HPR116-NS | 0.6 | 5.0 | 8.3 |

| Inducibility of CYP2B6 activity (bupropion hydroxylase activity) | Vmax value (nmol/h/mg proteins) | | |
|---|---|---|---|
| Induction ± Phenobarbital 1 mM | Un-induced | Induced | Fold induction |
| HPR116-S | 0.2 | 1.4 | 7.0 |
| HPR116-NS | 0.2 | 1.2 | 6.0 |

Observation: These results indicate that the induction profiles of HPR116-NS were similar to those of HPR116-S cells, since the major P450 activities and their responsiveness to three prototypical inducers were induced at comparable levels in both cell preparations.

Conclusion

HepaRG®-NS cells produced with new freezing and thawing process have the same trend as classical lot in terms of thawed viability and yield, as well as measured enzymatic activities and response to inducers.

Example 2

Feasibility Study of NS Process for Direct Thawing/Plating Primary Hepatocytes

In this Example, classic and improved processes, as described in Example 1 above, were carried out on primary hepatocytes. Cryopreserved primary human hepatocytes and rat hepatocytes were used for testing.

The cells were subjected to the classic method that generally involved, thawing cells in thawing/washing medium, centrifuge and then resuspend cells in seeding medium at an appropriate concentration. Other cryopreserved human hepatocytes and rat hepatocytes from the same lots were subjected to the improved method that generally involved thawing cells directly in thawing/seeding medium at an appropriate concentration based on pre-determined cell number, as described in Example 1. Both sets of cells were then seeded by thawing cells (without Percoll gradient centrifugation) using either the classical or improved process, followed by plating on a culture plate at the same cell density.

The plated cells were then observed for cell morphology, plateability, and metabolic activity.

The results are shown in the Table below.

TABLE

| Post-thaw viability and cell yield of Rat and Human hepatocytes (Classical (CL) vs invention method (NS)) | | | | | |
|---|---|---|---|---|---|
| | Cell freezing (M cells/vial) | Thawed viability (%) | Thawed yield (M/vial) | DMSO Dilution fold (X) | Final DMSO in seeding medium (%) |
| Cryopreserved rat hepatocytes | | | | | |
| HEP184133-CL | 10M/1 mL | 85 | 5.8 | 100 | 0 |
| HEP184133-NS | 10M/0.5 mL | 83 | 5.1 | 20.4 | 0.59 |
| Cryopreserved human hepatocytes | | | | | |
| HEP187254-CL | 10M/1 mL | 88 | 8.7 | 100 | 0 |
| HEP187254-NS | 10M/0.5 mL | 86 | 8.8 | 12.6 | 0.95 |

Figure 3:
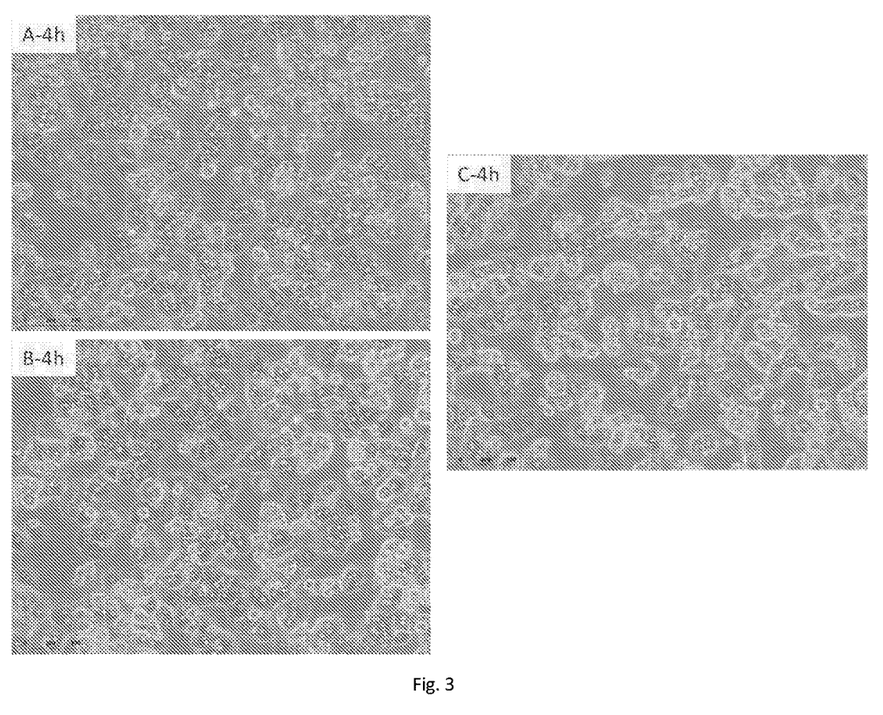
FIG. 3 shows images of cell monolayers from plating standard and no-spin processed rat primary hepatocytes at 4 hours post-plating from Example 2.
Figure 4:
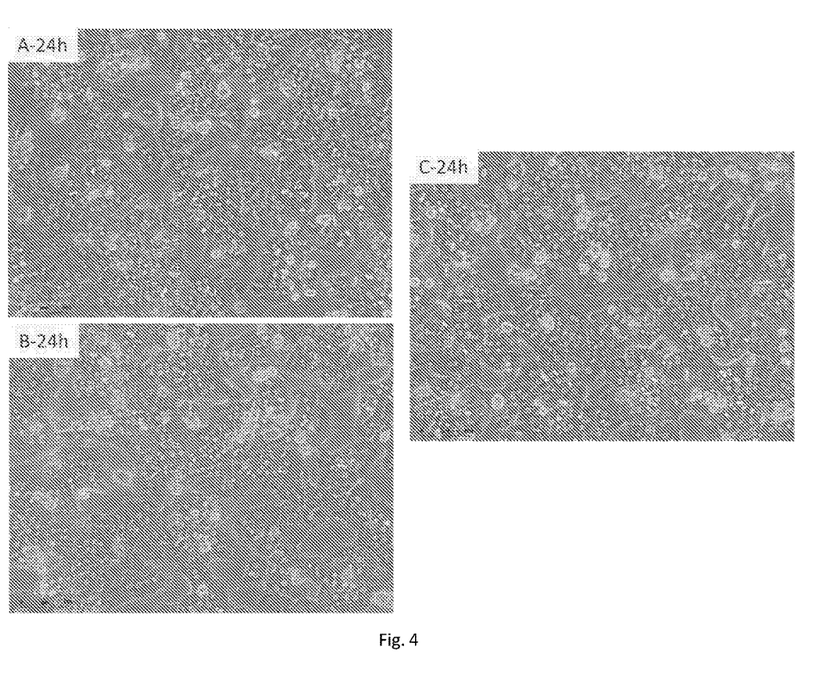
FIG. 4 shows images of cell monolayers from plating standard and no-spin processed rat primary hepatocytes at 24 hours post-plating from Example 2.

The results of plateability of thawed Rat SD hepatocytes: Classical (CL) vs invention method (NS) are shown in FIGS. 3-4. FIG. 3 shows cell monolayers, 4 hours post-plating. FIG. 3A shows HEP184133-CL (frozen cells at 1 mL/vial), subjected to classical thawing+spin-washing+plating. FIG. 3B shows HEP184133-NS (frozen cells at 0.5 mL/vial), subjected to classical thawing+spin-washing+plating. FIG. 3C shows HEP184133-NS (frozen cells at 0.5 mL/vial), subjected to the inventive thawing process+plating. FIG. 4 shows cell monolayers, after 1 day in short-term culture. FIG. 4A shows HEP184133-CL (frozen cells at 1 mL/vial), subjected to classical thawing+spin-washing+plating. FIG. 4B shows HEP184133-NS (frozen cells at 0.5 mL/vial), subjected to classical thawing+spin-washing+plating. FIG. 4C shows HEP184133-NS (frozen cells at 0.5 mL/vial), subjected to the inventive thawing process+plating.

Figure 5:
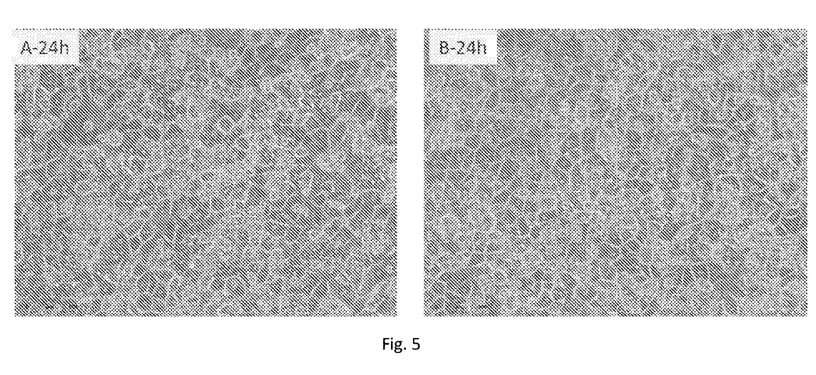
FIG. 5 shows images of cell monolayers from plating standard and no-spin processed human primary hepatocytes 24 hours post-plating from Example 2.
Figure 6:
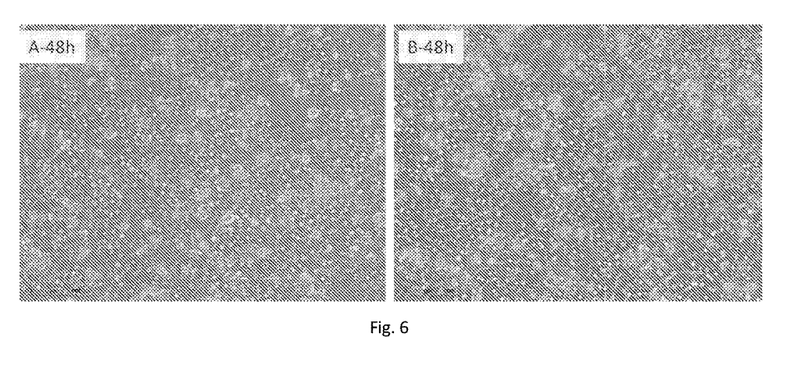
FIG. 6 shows images of cell monolayers from plating standard and no-spin processed human primary hepatocytes 48 hours post-plating from Example 2.

The results of plateability of thawed Human hepatocytes: Classical (CL) vs invention method (NS) are shown in FIGS. 5-6. FIG. 5 shows cell monolayers, 24 h after plating. FIG. 5A shows HEP187254-CL subjected to classical thawing+spin-washing+plating. FIG. 5B shows HEP187254-NS, subjected to the inventive thawing process+plating. FIG. 6 shows cell monolayers, 48 h after plating. FIG. 6A shows HEP187254-CL, subjected to classical thawing+spin-washing+plating. FIG. 6B shows HEP187254-NS subjected to the inventive thawing process+plating. As can be seen, the cell attachment efficiency of the inventive prepared cells was comparatively similar to the cells prepared from classical freezing, thawing and plating process.

The results of metabolic activity study are shown in the Table below. The metabolic activity of phase I was evaluated using P450 substrate cocktails. As can be seen, overall, the Vmax value of Phase I dependent activities were similar in both classic and NS methods.

| Metabolic Activity* (nmole/h/mg proteins) | P450 Enzyme | RAT SD Frozen Hepatocytes lot HEP184133 | | Human Frozen Hepatocytes lot HEP187254 | |
|---|---|---|---|---|---|
| | | Sample CL | Sample NS | Sample CL | Sample NS |
| Phenacetin O-deethylase activity | CYP1A2 | 1.1 | 1.3 | 0.4 | 0.4 |
| Midazolam 1' hydroxylase activity | CYP3A4/5 | 1.1 | 1.2 | 1.6 | 2.4 |
| Bupropion hydroxylase activity[a] | CYP2B6 | 0.2 | 0.2 | 0.2 | 0.3 |
| Dextrometorphan o demethylase activity | CYP2D6 | 1.1 | 1.5 | 0.4 | 0.5 |

*Cell monolayers after thawing & plating by either classic (CL) or non-spin method (NS) were incubated for 1 hour at 37° C. with the following substrates cocktails: phenacetin (200 µM), midazolam (50 µM), bupropion (100 µM) and dextrometorphan (100 µM). Metabolites formed were measured by LC-MS/MS. Activities are expressed as nmole/h/mg of protein.

Example 3

Tolerance of Percentage of DMSO in Hepatocyte NS Plating

In this Example, testing was carried out to determine the effect of different concentrations of DMSO (0 to 2%) on the cell plateability/attachment using the inventive, direct NS plating method.

Fresh human hepatocytes having 78% viability, corresponding generally to customary thawed cell viability, were plated with DMSO in concentrations ranging from 0 to 2%. The cells were plated without Percoll density gradient centrifugation for both classical and NS methods. The cell seeding density was 0.37 million cells/well (MW24 plate) for both classical & NS methods. The cells were evaluated for cell morphology, plateability, and metabolic activity.

Figure 7:
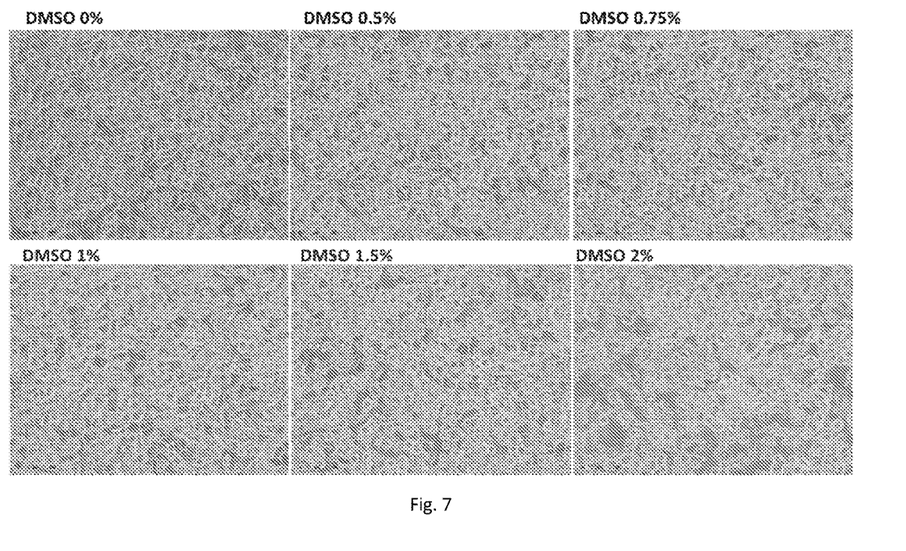
FIG. 7 shows images of cell monolayers from plating fresh hepatocytes in varying concentrations of DMSO at 20 hours post-plating from Example 3.
Figure 8:
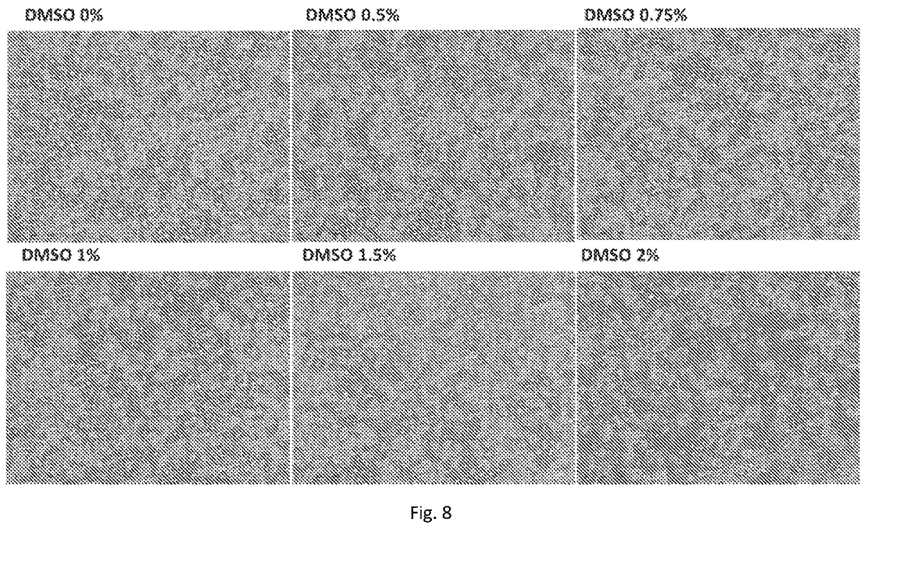
FIG. 8 shows images of cell monolayers from plating fresh hepatocytes in varying concentrations of DMSO at 48 hours post-plating from Example 3.

The results are shown in FIGS. 7-8. FIG. 7 shows cell monolayers, 20 h-post plating. FIG. 8 shows cell monolayers, 48 h post-plating in short-term culture. As can be seen from the Figures, the maximum tolerated DMSO percentage in hepatocyte-NS plating medium for cell attachment should be less than 1% (v/v). The recommended final concentration of DMSO is less than 0.8% for using NS direct cell thawing/plating. The DMSO, as a cryoprotectant included in freezing medium, has been tested at final concentrations up to 2% in the cell plating medium.

The results of the metabolic activity study are shown in the Table below for the plated fresh hepatocytes.

Example 4

Plateability of a New Lot of Frozen Human Hepatocytes: CL vs NS

Figure 9:
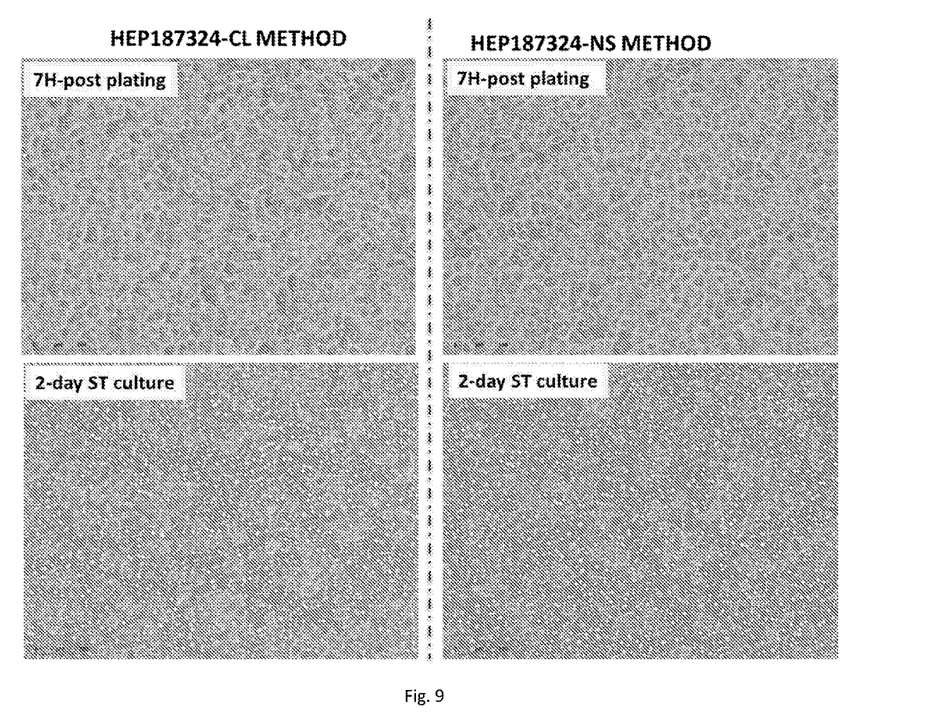
FIG. 9 shows images of cell monolayers from plating standard and no-spin processed hepatocytes at 7 hours and 2 days post plating from Example 4.

A new lot of frozen human hepatocytes (HEP187324) were prepared using the classical and no-spin methods described above, and then plated. The results are shown in FIG. 9.

Example 5

Applicability of Using NS Method for Frozen Hepatocytes Prequalified as Suspension Cells Cells from the same lot used in Example 4 where tested for the ability to use the NS-processed cells directly in suspension assays. In the art, cryopreserved hepatocytes can be pre-qualified as plateable or suspension cells according to their attachment efficiency & monolayer confluency after thawing and plating. Thus the pre-qualified cryopreserved hepatocytes can be then chosen for either suspension or plated assays according to the desired in vitro ADME/Tox applications. This Example, in combination with Example 4, demonstrates the ability of the NS method to be used for cells designated for either plated or suspension assays. As demonstrated by the data above, hepatocytes pre-qualified as plateable can be processed using the inventive no-spin process, and the resulting plated cells show similar cell viability, plateability, metabolism activity compared to plated cells prepared from classic thawing, washing, and plating processes.

Figure 10:
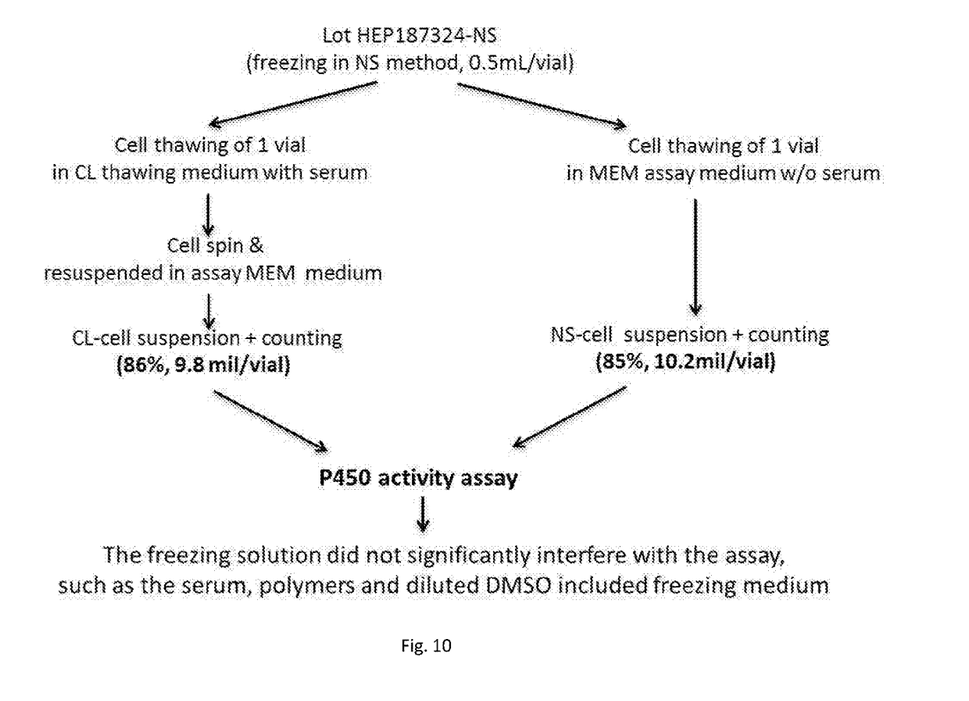
FIG. 10 shows a process flow for assessing thawed viability and activity of cells pre-qualified for suspension assays from Example 5.

The work here demonstrates that suspension qualified hepatocytes can be also used in the NS process. In the present Example, the frozen cells were thawed directly in an assay working buffer (e.g., phenol red-free MEM). FIG. 10 illustrates a flow-chart for assessing the thawed viability and activity of human hepatocytes in classic thawing medium vs phenol-red free assay medium. The results of post-thaw cell viability and yield of frozen human hepatocytes are shown in the Table below.

| Cryopreserved human hepatocytes | Thawed viability (%) | Thawed yield (M/vial) | Final DMSO in assay medium (%) |
|---|---|---|---|
| HEP187324-CL | 86 | 9.8 | 0 |
| HEP187324-NS | 85 | 10.2 | 0.86 |

For the CL sample, cells were firstly thawed in classical thawing medium and spin washed and then resuspended in an assay medium for cell counting. For the NS sample, cells

| Metabolic Activity (nmole/h/mg proteins) | P450 Enzyme | Human fresh hepatocytes: after plating in medium ± DMSO | | | | | |
|---|---|---|---|---|---|---|---|
| | | DMSO 0% | DMSO 0.5% | DMSO 0.75% | DMSO 1% | DMSO 1.5% | DMSO 2% |
| Phenacetin O-deethylase activity | CYP1A2 | 1.0 | 0.8 | 0.8 | 1.0 | 0.9 | 0.9 |
| Midazolam 1' hydroxylase activity | CYP3A4/5 | 3.8 | 3.2 | 2.7 | 3.3 | 3.6 | 2.4 |
| Bupropion hydroxylase activity | CYP2B6 | 0.2 | 0.1 | 0.2 | 0.2 | 0.3 | 0.2 |
| Dextrometorphan o demethylase activity | CYP2D6 | 0.4 | 0.3 | 0.3 | 0.3 | 0.4 | 0.3 | were directly thawed in an assay medium (MEM, w/o phenol red) for cell counting. Comparable thawed viabilities and cell numbers were obtained for both methods.

The resulting metabolic activity is shown in the Table below.

| Metabolic Activity (nmole/h/mg proteins) | P450 Enzyme | Human cryopreserved hepatocytes lot HEP187324 | |
|---|---|---|---|
| | | Sample CL | Sample NS |
| Phenacetin O-deethylase activity | CYP1A2 | 2.0 | 2.1 |
| Midazolam 1' hydroxylase activity | CYP3A4/5 | 1.4 | 1.1 |
| Bupropion hydroxylase activity | CYP2B6 | 0.6 | 0.6 |
| Dextromethorphan o demethylase activity | CYP2D6 | 0.9 | 0.7 |

For the CL sample, cells were firstly thawed in classical thawing medium and spin washed and then resuspended in an assay medium (MEM w/o phenol red) for metabolic activity assay. For the NS sample, cells were directly thawed in an assay medium (MEM, w/o phenol red) for metabolic activity assay. Comparable P450 activities were observed for both samples. The data demonstrates that the components of the freezing solution did not significantly interfere with the assay, such as the serum and polymers included freezing medium, even reduced from 10% to 0.5% after 20-fold dilution.

Example 6

Figure 11:
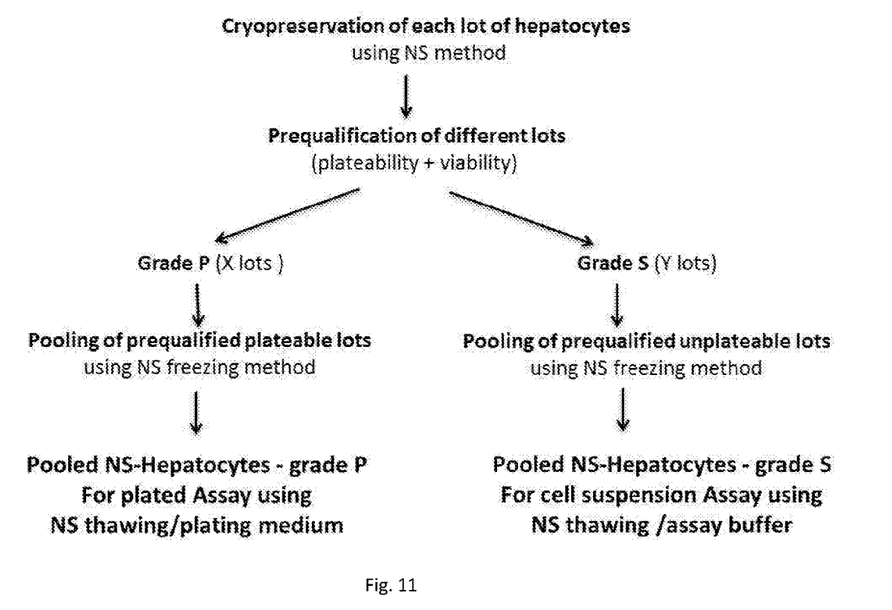
FIG. 11 shows a process for utilizing the no-spin methodology in preparing pooled preparations of hepatocytes.

FIG. 11 shows a flow-chart of a NS procedure for developing pooled Hepatocytes suitable for either plated assay or suspension assay.

What is claimed:

1. A method for thawing and recovery of cryopreserved hepatocytes, said method comprising:
providing a concentrated composition of cryopreserved hepatocytes comprising a first amount of hepatocytes dispersed in a freezing solution, said freezing solution comprising a cryoprotectant dispersed in medium;
thawing said concentrated composition of cryopreserved hepatocytes to yield a thawed composition of hepatocytes, wherein said thawed composition of hepatocytes comprises thawed hepatocytes and cryoprotectant dispersed in a medium; and
directly plating said thawed composition of hepatocytes or directly suspending said thawed composition of hepatocytes in a suspension assay, without removal of said cryoprotectant.

2. The method of claim 1, wherein said directly plating or directly suspending are carried out without subjecting said thawed composition of hepatocytes to centrifugation.

3. The method of claim 1, wherein said directly plating or directly suspending are carried out without subjecting said thawed composition of hepatocytes to washing with fresh medium or thawing medium.

4. The method of claim 1, wherein said directly plating or directly suspending are carried out without plating and counting said hepatocytes in said thawed composition of hepatocytes.

5. The method of claim 1, wherein said concentrated composition of cryopreserved hepatocytes is provided in a cryopreservation container, said thawing comprising:
warming said cryopreservation container until said concentrated composition of cryopreserved hepatocytes is at least partially thawed; and
diluting said at least partially-thawed concentrated composition of hepatocytes with prewarmed thawing medium to achieve a desired hepatocytes concentration for said plating or said suspending.

6. The method of claim 5, wherein said diluting comprises adding said thawing medium to said cryopreservation container.

7. The method of claim 5, wherein said diluting comprises transferring said at least partially-thawed concentrated composition of hepatocytes to a second container containing said prewarmed thawing medium.

8. The method of claim 5, wherein said diluting comprises transferring said at least partially-thawed concentrated composition of hepatocytes to a second container and adding said prewarmed thawing medium to said second container.

9. The method of claim 1, wherein said concentrated composition of cryopreserved hepatocytes is provided in a cryopreservation container, said thawing comprising adding prewarmed thawing medium to said cryopreservation container to simultaneously thaw and dilute the hepatocyte composition to achieve a desired hepatocyte concentration for said plating or said suspending.

10. The method of claim 1, wherein said thawing comprises mixing said concentrated composition of cryopreserved hepatocytes with pre-warmed suspension assay buffer or medium.

11. The method of claim 10, wherein said concentrated composition of cryopreserved hepatocytes is at least partially thawed using a warm water bath before mixing with said pre-warmed suspension assay buffer.

12. The method of claim 1, wherein said directly plating comprises seeding said thawed composition of hepatocytes on a culture plate or culture support as a cell monolayer.

13. The method of claim 1, wherein said first amount of hepatocytes is a concentrated cell suspension comprising from about 2 million hepatocytes/mL to about 200 million hepatocytes/mL of said cell suspension.

14. The method of claim 13, wherein said concentrated cell suspension and freezing solution are mixed in a range of from about 0.1:1.9 to about 1.9:0.1 by volume in said concentrated composition of cryopreserved hepatocytes.

15. The method of claim 1, wherein said cryoprotectant is ethylene glycol, propylene glycol, dimethyl sulfoxide (DMSO), fetal bovine serum (FBS), propanediol, glycerol, or a mixture of the foregoing.

16. The method of claim 15, wherein said cryoprotectant is DMSO, said freezing solution comprising from about 5% to about 20% (v/v) DMSO.

* * * * *